United States Patent

Truax

[11] Patent Number: 5,176,517
[45] Date of Patent: Jan. 5, 1993

[54] DENTAL UNDERCUT APPLICATION DEVICE AND METHOD OF USE

[75] Inventor: Lloyd H. Truax, Rochester, Minn.

[73] Assignee: Tru-Tain, Inc., Rochester, Minn.

[21] Appl. No.: 782,159

[22] Filed: Oct. 24, 1991

[51] Int. Cl.⁵ .............................................. A61C 13/12
[52] U.S. Cl. ........................................ 433/180; 433/9; 433/215; 433/226
[58] Field of Search ................ 433/3, 9, 18, 180, 181, 433/215, 218, 226

[56] References Cited

U.S. PATENT DOCUMENTS

| | | | |
|---|---|---|---|
| Re. 15,265 | 1/1922 | Roach | 433/46 |
| 1,367,477 | 2/1921 | Homer | 433/218 |
| 1,410,311 | 3/1922 | Howe | 433/40 |
| 2,889,625 | 6/1959 | Saffir | 433/180 |
| 3,357,104 | 12/1967 | Greene et al. | 433/40 |
| 3,521,355 | 7/1970 | Pearlman | 433/3 |
| 3,745,653 | 7/1973 | Cohl | 433/9 |
| 3,835,538 | 9/1974 | Northcutt | 433/9 |
| 4,398,887 | 8/1983 | Balde et al. | 433/218 |
| 4,445,861 | 5/1984 | Klepacki | 433/9 |
| 4,449,928 | 5/1984 | von Weissenfluh | 433/40 |
| 4,768,957 | 9/1988 | Segura | 433/181 |
| 4,773,857 | 9/1988 | Herrin | 433/9 |
| 4,834,654 | 5/1989 | Nussbaum | 433/141 |
| 4,881,898 | 11/1989 | Harvey, Sr. et al. | 433/215 |
| 4,971,558 | 11/1990 | Jacobi | 433/226 |
| 5,040,981 | 8/1991 | Oliva | 433/141 |

Primary Examiner—John J. Wilson
Attorney, Agent, or Firm—Merchant, Gould, Smith, Edell, Welter & Schmidt

[57] ABSTRACT

A dental undercut application device for producing an undercut on the surface of a tooth for securing a dental appliance. The application device contains an undercut or applique with a curved front side for engagement with the surface of the tooth and a stem on the back side attached to a locator tab. The locator tab can be grasped when applying the adhesive to the front side of the undercut and for locating the undercut on the surface of the tooth while the adhesive cures. When the undercut is secured to the tooth, the stem is cut and the tab removed. The back side of the undercut may then be smoothed to match the contour of the tooth. Clasps on removable orthodontic appliances or removable partial dentures engage with the undercut to retain the dental appliance or denture in the patient's mouth.

17 Claims, 2 Drawing Sheets

DENTAL UNDERCUT APPLICATION DEVICE AND METHOD OF USE

FIELD OF THE INVENTION

The present invention relates to a method and apparatus for producing an undercut area or applique on the surface of a tooth for securing a variety of dental appliances. In particular, an applique having a detachable tab portion is provided for attaching the applique to the surface of a tooth. Following the removal of the detachable tab portion, the remaining applique provides a variation in the contour of the outer surface of a tooth for securing removable dental appliances thereto.

BACKGROUND OF THE INVENTION

Dental appliances or prostheses, such as removable orthodontic devices or partial dentures, are typically held in place by securing the appliance to adjacent teeth. An Adam's, ring or "C" clasp is commonly used for this purpose. The clasp is a wire structure which wraps around adjacent teeth, generally along the gum line, in order to provide stable and reliable attachment of the dental appliance.

However, this configuration does not secure a removable dental appliance and can irritate the gum tissue. In certain circumstances, the crown of a tooth is prepared whereby a portion of the crown is removed and a dental crown is place on the tooth to provide an undercut surface. This method, however, is destructive to the tooth and expensive.

The method and apparatus of the present invention produces a properly contoured undercut on the surface of the tooth without damaging the tooth. Various removable dental prostheses and appliances can be held securely in place using the method and apparatus of the present invention.

SUMMARY OF THE INVENTION

The present invention relates to a method and apparatus for attaching an undercut to the surface of a tooth for securing various dental appliances.

The apparatus of the present invention is a dental undercut application device for attaching an undercut to an outer surface of a tooth, the device comprising an applique having a back side and a curved front for engagement with the outer surface of the tooth. Because of the relatively small size of the applique or undercut, a locator tab is attached to the back side of the undercut. The locator tab is used for holding the undercut while the front side is coated with an adhesive, and/or for positioning the undercut on the surface of the tooth. After the adhesive has cured, the tab is typically removed and the back side of the undercut, where a portion of the tab attachment piece may remain, is smoothed with abrasive materials or tools.

The method of the present invention includes a method of attaching a dental undercut to an outer surface of a tooth, the method comprising the steps of: providing a dental undercut application device which includes an applique having a back side, a curved front side for engagement with the outer surface of the tooth, and a tab attachment portion interconnected with the back side. A locator tab is interconnected to the tab attachment portion for grasping the application device securing the front side of the applique to the outer surface of the tooth. The locator tab is separated from the applique when the applique is secured to the tooth. Preferably, the applique is secured to the tooth with an FDA-approved adhesive material.

The method of the present invention preferably includes preparing the surface of the tooth for receiving the applique or undercut, grasping the locator tab while the front surface of the undercut is coated with an adhesive, positioning the undercut on the surface of the tooth. The stem between the undercut and the tab is cut and any remaining portions of the stem are removed from the back side of the undercut so that its contour matches the surface of the tooth.

The present method of removably securing a removable dental appliance within a patient's mouth, where the patient's mouth includes at least one tooth comprising the step of attaching at least one dental undercut to the at least one tooth in the patient's mouth. The dental appliance is removably secured within the patient's mouth by sliding a securing portion of the removable appliance over the dental undercut attached to at least one tooth, wherein the dental undercut will provide resistance to the removal of the removable dental appliance when the appliance is removed from the patient's mouth.

As used in the present specification, the term "outer surface", when used in reference to a tooth, means any outer surface of the tooth, including without limit the buccal, lingual, distal or mesial surfaces of the tooth.

Finally, the applique of the present invention can be removed when the dental appliance is no longer required, returning the surface of the tooth to its original condition.

DETAILED DESCRIPTION OF THE PREFERRED EMBODIMENT

Figure 1:
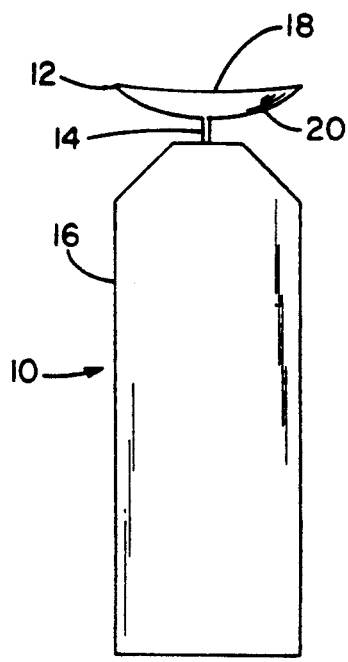
FIG. 1 is a top view of the dental undercut application device of the preferred embodiment of the present invention.

FIG. 1 illustrates the dental undercut application device 10 of the preferred embodiment of the present invention. The undercut or applique 12 is attached to the tab 16 by an elongated stem 14. In the preferred embodiment of the present invention the undercut application device 10 is formed of a single homogeneous piece of plastic produced through an injection molding process. Lexan TM, an FDA-approved polycarbonate plastic made by General Electric Corporation, is known to be suitable for this purpose. However, it will be recognized by those skilled in the art that the dental undercut application device 10 of the present invention could be formed from a variety of materials such as FDA-approved ceramics or metals. Further, the tab 16 and stem 14 portion of the dental undercut application device 10 do not necessarily need to be made from the same material. For example, a ceramic undercut could be connected to a plastic stem and tab with a suitable adhesive.

The front side 18 of the undercut 12 is generally concave in shape to match the contour of the tooth surface Likewise, the back side 20 of the undercut 12 may be curved so that the undercut 12 will be properly contoured with the surface of the tooth.

Figure 2:
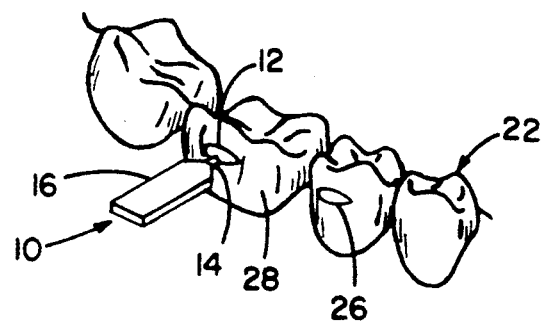
FIG. 2 is a perspective of a patient's mouth showing the dental undercut application device for applying the applique or undercut of the present invention to the outer surface of a tooth.

FIG. 2 is a perspective view of several teeth 22 to which a first undercut or applique 12 is being applied to the surface of the tooth 28 with a suitable adhesive (not shown). FIG. 2 also illustrates a second undercut 26 which has been previously applied. Although FIG. 2 illustrates use of the dental undercut application device 10 of the present invention on the buccal or front view of the teeth, it will be understood by those skilled in the art that the dental undercut application device 10 of the present invention may be applied to any surface of the tooth, including the occlusal or labial surfaces.

The method of the present invention requires that the surface of the tooth 28 be cleaned with a suitable polish or abrasive prior to attaching the undercut 12 of the present invention. The tooth surface 28 is then acid etched in order to create a good bonding surface for the adhesive (not shown) Reliance Gel Etching Agent from Reliance Corporation ® is known to be suitable for this purpose. The etching gel is 50 percent phosphoric acid. The etching gel is applied to the tooth for approximately 60 seconds. The tooth surface 28 is then rinsed with sufficient water to neutralize the etching agent and allowed to dry. A plastic conditioner may be placed on the front side 18 of the undercut 12 and the tooth surface 28 prior to application of the adhesive.

Because the undercut 12 is extremely small, the operator grasps the tab 16 with a hemostat while applying the adhesive to the front side 18 of the undercut 12. While still holding the tab 16, the operator places the undercut 12 against the surface of the tooth 28. Typically, the undercut 12 is located in approximately the middle or cervical one third of the buccal or labial surface of the tooth. One adhesive known to be suitable for this purpose is made from diacrylate resins available from Reliance Corporation. The adhesive cures when exposed to electromagnetic energy. The Visilux TM light cure unit from 3M Corporation is known to be suitable for curing the adhesive.

The adhesive cures in approximately 60 seconds. After the operator has determined that the undercut 12 is securely anchored to the surface of the tooth 28, the stem 14 is cut using a ligature wire cutter and the back side 20 of the undercut 12 is smoothed with a diamond stone or sandpaper disk. Because the undercut 12 is extremely small and its contour is smoothed matches the surface of the tooth, the undercut 12 does not significantly reduce the aesthetics of the tooth.

Figure 3:
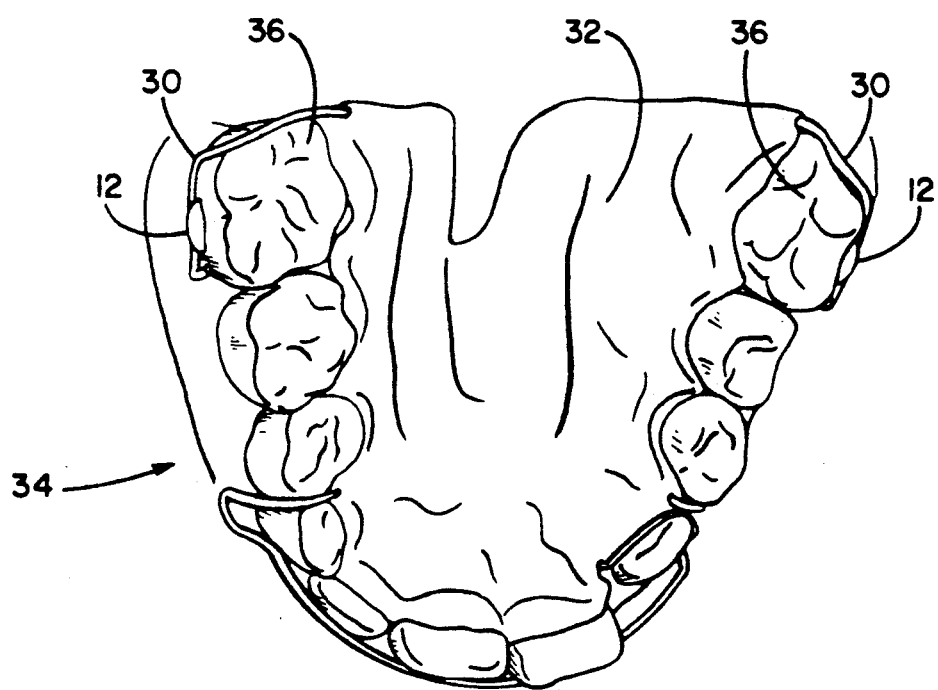
FIG. 3 is a perspective view illustrating the operation of the applique or undercut retaining a typical dental appliance.

FIG. 3 illustrates a perspective view of a dental appliance 32 anchored to mouth section 34 with a series of wire clasps 30. The clasps 30 are formed to engage with the undercuts 12 previously attached to the surface of the teeth 36. Because the clasp 30 does not need to be as accurately fitted around the contour of the teeth 36, the dental appliance 32 is much less expensive to manufacture and can be more easily fitted to the individual patient. Further, the clasps 30 do not need to wrap around the teeth 36 along the gum line. Rather, the clasps 30 only extent around two sides of the teeth 36 and engage the undercut 12 on the surface of the teeth 36 above the gum line, providing greater comfort to the patient and better retention of the removable appliance.

It will be understood that the present invention is not limited to the examples discussed above, but may be changed or modified without departing from the spirit or scope of the invention. For example, the back side of the applique does not necessarily have to match the contour of the tooth surface. It may be desirable in some circumstances for the undercut to be a variety of shapes which may be more suited to retaining the dental appliance or partial denture. Therefore, fastening means, such as a hook or an exaggerated ridge for engaging with the clasp, may be formed on the back side of the undercut. Metal or ceramic undercuts are probably best suited for an embodiment with attachment means on the back side of the undercut.

What is claimed is:

1. A dental undercut application device for attaching an undercut to an outer surface of a tooth, the outer surface having a contour, said dental undercut application device comprising:

an applique having a back side, a curved front side for attachment to the outer surface of the tooth, and a removable tab attachment portion interconnected with said back side, said back side having a contour generally similar to the contour of the tooth; and removable locator tab means interconnected to said removable tab attachment portion for positioning the applique upon the tooth, wherein said tab means are removable from said applique.

2. The dental undercut application device of claim 1 wherein said curved front side is a concave surface.

3. The dental undercut application device of claim 1 wherein said applique, said tab attachment portion and said locator tab means are a single, integral piece of homogeneous material, wherein the homogeneous material is a plastic material.

4. The dental undercut application device of claim 3 wherein the plastic material is polycarbonate.

5. A dental applique for providing an undercut area on an outer surface of a tooth for securing a dental appliance thereto, the dental applique comprising:

an applique member having a back side, a curved front side for attachment to the outer surface of the tooth and a removable stem interconnected with said back side, said back side having a contour generally similar to the contour of the tooth; and adhesive means for attaching said applique to the tooth.

6. The dental applique of claim 5 wherein said front side is a concave surface.

7. A method of attaching a dental undercut to an outer surface of a tooth, said method comprising the steps of:

providing a dental undercut application device including: an applique having a back side, a curved front side for engagement with the outer surface of the tooth, and a tab attachment portion interconnected with said back side and locator tab means interconnected to said tab attachment portion for grasping said application device;

securing the front side of the applique to the outer surface of the tooth; and separating said locator tab means from the applique when the applique is secured to the tooth.

8. The method of claim 7 wherein the step of securing includes grasping said locator tab means, applying an adhesive to said curved front surface of the applique, and pressing said applique and said adhesive against the outer surface of the tooth for a sufficient period of time to permit said adhesive to secure said applique to the tooth.

9. The method of claim 8 wherein the step of securing is preceded by a step preparing the outer surface of the tooth for receiving said adhesive.

10. The method of claim 9 wherein the step of preparing includes cleaning the outer surface of the tooth with abrasive materials.

11. The method of claim 9 wherein the step of preparing includes etching the outer surface of the tooth with an acid-containing composition.

12. The method of claim 7 wherein the step of separating includes the step of removing any remaining portion of said tab attachment portion so that said back side is smooth proximate an area thereof where said tab attachment portion was previously attached.

13. A method of attaching a dental undercut to a generally unaltered outer surface of a tooth, said method comprising the steps of:
providing an applique member having a back side, a curved front surface for engagement with the generally unaltered outer surface of the tooth and a stem interconnecting a locator tab with said back side;
coating said front surface of the undercut with an adhesive;
placing said undercut against the generally unaltered outer surface of the tooth for a period of time sufficient to allow said adhesive to secure the undercut to the generally unaltered outer surface of the tooth;
separating the locator tab from said undercut proximate the stem; and
removing any remaining portions of said stem from the back side of the undercut to create a generally smooth surface.

14. The method of claim 13 further including the step of polishing the surface of the tooth with an abrasive prior to securing said undercut.

15. The method of claim 13 further including the step of etching the surface of the tooth with an acid-containing composition prior to the step of placing said undercut against the generally unaltered outer surface of the tooth.

16. A method of removably securing a removable dental appliance within a patient's mouth, the appliance having a securing portion, the patient's mouth including at least one tooth, the tooth having a generally unaltered outer surface, said method comprising the steps of:
attaching at least one dental undercut to the generally unaltered outer surface of at least one tooth in the patient's mouth; and
removably securing the removable dental appliance within the patient's mouth, wherein the step of removably securing includes sliding a securing portion of the removable appliance over said dental undercut attached to the at least one tooth, wherein the dental undercut will provide resistance to the removal of the removable dental appliance when an attempt is made to remove the appliance from the patient's mouth.

17. The method of claim 16 wherein the step of attaching includes:
providing a dental undercut application device including: an applique having a back side, a curved front side for engagement with the outer surface of the tooth, and a tab attachment portion interconnected with said back side and locator tab means interconnected to said tab attachment portion for grasping said application device;
securing the front side of said applique to the outer surface of the tooth; and
separating said locator tab means from said applique when the applique is secured to the tooth.

* * * * *